United States Patent [19]

Pierre et al.

[11] 4,036,697
[45] July 19, 1977

[54] KINETIC ASSAY FOR ALPHA-AMYLASE

[75] Inventors: Kenneth Jonas Pierre; Ker-Kong Tung; Henriette Nadj, all of Vista, Calif.

[73] Assignee: Beckman Instruments, Inc., Fullerton, Calif.

[21] Appl. No.: 657,976

[22] Filed: Feb. 13, 1976

[51] Int. Cl.$^2$ .................... G01N 33/00; G01N 31/14
[52] U.S. Cl. ................................ 195/99; 195/103.5 R
[58] Field of Search ............... 195/103.5 R, 103.5 C, 195/99

[56] References Cited

U.S. PATENT DOCUMENTS 3,879,263  4/1975  Adams .................... 195/103.5 R

FOREIGN PATENT DOCUMENTS 2,349,819  10/1973  Germany

OTHER PUBLICATIONS

Kamagawa et al. "An Enzymatic Method for the Determination of Maltose in the Presence of Other Oligosaccharides" Anal. Biochem. 57 (1974) pp. 303-305.
Belocopitow et al. "A Specific Method for the Quantitative Determination of $\beta$–Glucose-1-Phosphate" Anal. Biochem. 53 (1973) pp. 108-114.

*Primary Examiner*—A. Louis Monacell
*Assistant Examiner*—C. A. Fan
*Attorney, Agent, or Firm*—R. J. Steinmeyer; P. R. Harder; R. S. Frieman

[57] ABSTRACT

A kinetic assay is provided for measuring alpha-amylase content in aqueous solutions. The assay is based on the following reactions:

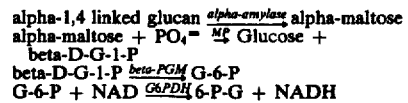

The concentration of alpha-amylase is determined by measuring the rate of increase in absorbance associated with the production of NADH which is a measure of the activity of alpha-amylase.

A novel reagent system is used with the assay and comprises:
  a polysaccharide having glucose molecules primarily connected through alpha 1,4 linkage
  maltose phosphorylase (MP)
  Phosphate ions (PO$_4$$^-$)
  beta-nicotinamide-adenine dinucleotide (NAD) or beta-nicotinamide-adenine dinucleotide phosphate
  beta-D-phosphoglucomutase (Beta-PGM)
  Glucose-6-phosphate Dehydrogenase (G6PDH)

37 Claims, No Drawings

KINETIC ASSAY FOR ALPHA-AMYLASE

BACKGROUND OF THE INVENTION

This invention relates to reagents and methods for determining alpha-amylase concentration in aqueous solutions such as serum and urine.

Alpha-amylase is an enzyme produced by the human body and is found in fluids such as blood, urine and saliva. It is not entirely certain what part of the body produces alpha-amylase, but it is clear that when the body is healthy, the concentration of alpha-amylase present in human fluids will vary over a range of values, and when the body is suffering from certain pathological conditions the alpha-amylase concentration will be higher or lower than the range existing when the body is healthy. For example, when a person has pancreatitis, mumps, or pancreatic cancer, the alpha-amylase concentration will be much greater than its level in the absence of such conditions. Liver diseases may produce alpha-amylase concentrations that are lower than otherwise.

Techniques for determining alpha-amylase concentrations generally involve the use of starch because of the catalytic effect of alpha-amylase on the hydrolysis of the 1,4 linkages of the amylose and amylopectin fractions of starch. If this hydrolysis is left to go to completion, the alpha-amylase will progressively degrade the starch into glucose, maltose, and oligosaccharides. Certain techniques have attempted to correlate the decrease in the turbidity or viscosity of an aqueous starch solution after amylose hydrolysis with the resultant alpha-amylase concentration.

Other techniques utilize the quantity of reducing substances produced by the alpha-amylase-starch reaction as a measure of alpha-amylase concentration, or utilize the rate of dye release from a dyed starch by alpha-amylase as a measure of alpha-amylase concentration.

Enzymatic technique have also been developed to measure alpha-amylase concentration by using alpha-amylase and other enzymes to hydrolyze starch into glucose which is then measured through coupled enzymatic reactions. This approach, however, is not satisfactory because of the presence in many assay specimens of glucose which will react through the coupled enzymatic reactions to produce easily detectable product in addition to that produced by enzymatic starch hydrolysis. The concentration of this endogenous glucose is generally significant with respect to the amount of glucose usually produced by the enzymatic hydrolysis technique; and as a result, such pre-existing glucose must be eliminated from the assay specimen before the assay is conducted.

Another technique is the iodometric method which utilizes the well known reaction between iodine and starch to form a blue color. When a blue colored starch-iodine solution is hydrolyzed with alpha-amylase, the blue color decreases as the alpha-amylase degrades the starch. The change in color of the blue starch-iodine solution is thus some measure of alpha-amylase concentration. This technique, however, has not been considered reliable or sufficiently definite because it is believed that the change in color does not bear a linear relationship to the concentration of alpha-amylase.

All of the foregoing techniques, while sufficient to yield a general indication of alpha-amylase concentration, are not entirely satisfactory because they either do not lend themselves to precise scientific measurements and/or are too time-consuming.

SUMMARY OF THE INVENTION

It is therefore an object of the present invention to provide a new set of reagents and a new method for using these reagents which will overcome the problems associated with prior techniques for determining alpha-amylase concentrations.

Another object of the present invention is to provide a new procedure for determining alpha-amylase concentrations which can be performed quickly, simply, reliably and with reproducible results.

These objects are achieved by the invention disclosed and claimed hereinafter which is a novel kinetic technique for measuring alpha-amylase concentrations in aqueous solutions which is based on the following reactions:

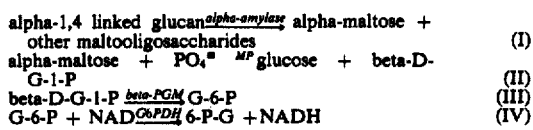

wherein the concentration of alpha-amylase in the aqueous solution is determined by measuring the rate of production of NADH which provides a measure of alpha-amylase concentration. The following abbreviations are employed in the above reactions and hereinafter:

ABBREVIATIONS

PO$_4^=$ —phosphate ion
MP —maltose phosphorylase
beta-D-G1P —beta-D-glucose-1-phosphate
beta-PGM—beta-D-phosphoglucomutase
G-1, 6-diP —D-glucose-1,6-diphosphate
G-6-P—glucose-6-phosphate
6-PG—6-phosphogluconate
G6PDH—glucose-6-phosphate dehydrogenase
6PDH—6-phosphogluconate dehydrogenase
NAD—beta-nicotinamide-adenine dinucleotide
NADH—reduced form of beta-nicotinamide-adenine dinucleotide The reagent system of the present invention contains the starting material of reaction I, alpha-1,4 linked glucan, and all of the constituents except alpha-amylase, needed to make all of the four reactions proceed as indicated, i.e., phosphate ions, MP, beta-PGM, and G6PDH. This reagent system may be provided and used as one mixture, or it may be provided in a kit consisting of a plurality of reagents each of which contain one or more of the ingredients of the reagent system which are all mixed together when the reagents are used in the alpha-amylase assay of the invention. All of the aforesaid ingredients of said reagent system appear to be stable as one mixture and thus it is preferred that the reagent system be provided as one mixture inasmuch as it is easier to work with one reagent rather than a plurality.

EMBODIMENTS OF THE INVENTION

With respect to the first reaction employed by the present invention:

the alpha-1,4 linked glucan may be any polysaccharide made up primarily of glucose wherein the glucose molecules are mainly connected through alpha-1,4 linkages which can be attacked by the alpha-amylase. Exemplary of such polysaccharides are starch, amylopectin, amylose, glycogen, dextrin and their degraded products, and homologs of maltooligosaccharides such as maltotriose, maltotetraose and maltopentaose or mixtures thereof.

Starch is the preferred form of said glucan because it offers the best combination of solubility, low expense, recovery and stability. Superlose 500 is the brand name of a starch which is used in the preffered embodiment of the invention. This starch has good cold water solubility, gives better response and linearity than other starches, yields good reproducibility, and is non-turbid in solution. Superlose 500 is a modified amylose distributed by Stein-Hall Company of New York City. Superlose 500 is a white, granular material having a moisture content of about 10 percent, a pH of 7, and a film tensile strength in excess of 8,000 pounds per square inch. The viscosity of Superlose 500 in Brookfield cps at 150° F is 185 for 14% solids, 55 for 10% solids, and 10 for 5% solids. At 75° F the viscosity is 2,000 for 14% solids, 275 for 10% solids, and 30 for 5% solids. Superlose 500 dissolves easily in water at room temperature in contrast to most starches which require some degree of agitation and/or heating before passing into solution. Superlose 500 is made from the modified amylose fraction of potato starch and contains so significant amount of the amylopectin fraction of starch.

GR brand starch is the brand name of another starch which may be used in the preferred embodiment. GR brand starch is distributed by E. Merck Company of 500 Executive Blvd., Elmsford, New York and manufactured by Merck European of Darmstadt, Germany. This starch is dialyzed prior to use and has the following characteristics: maximum sulfate ash of 7 weight percent; 10% by weight loss on drying; 1 gram of GR starch has a reducing power equivalent to 7 milligrams of maltose; pH of between 6.5 and 7.5, and a favorable sensitivity test.

According to the present invention, it is necessary that the amount of alpha-amylase be rate-limiting. Thus, the amounts of the other constituents of the reagent system of the present invention should be present in suitable amounts to ensure that the observed reaction rate for the complete assay system is characteristic of and determined by the rate of the alpha-amylase catalyzed reaction (reaction I). For the assay of aqueous solutions of human serum or urine, it is preferred to use a concentration of between about 1.0 to about 20 grams of an alpha-1,4 linked glucan per liter of reagent. A glucan concentration of about 5 grams per liter of reagent is used in the preferred embodiment.

With regard to the second reaction employed by the present invention:

alpha-maltose + phosphate $\xrightarrow{MP}$ Glucose + beta-D-Glu-1-P    (II)

the alpha-maltose produced by the first reaction is reacted with phosphate ions using maltose phosphorylase as an enzymatic catalyst to produce glucose and beta-D-glucose-1-phosphate.

The phosphate ions are supplied from any source compatible with the reagent system of the present invention. Inorganic phosphates are an example of such source. The phosphate used in the preferred embodiment is a mixture of $K_2HPO_4$ and $KH_2PO_4$ whic forms a buffered solution at a pH of about 6.5 which is optimum.

The concentration of phosphate ions should be at a level to ensure that alpha-amylase is the rate-limiting compound. However, it is desirable to have not too high a concentration of phosphate ions because large concentrations may inhibit the activity of the beta-PGM enzyme. It is preferred to have about 0.01 and about 0.1 molar concentration of inorganic phosphate, with about 0.025 molar being the most preferred amount for the assay of serum.

Maltose phosphorylase is an enzyme which catalyzes the reaction of alpha-maltose and inorganic phosphate. At least about 200 International Units (IU) of this enzyme per liter of reagent is required, but about 1000 IU per liter is preferred.

The preferred source of maltose phosphorylase is a strain of the microorganism *Lactobacillus brevis* (ATCC8287) which has been cultured by Beckman Instruments, Inc., Microbics Operations of Carlsbad, California and the enzyme has been extracted and purified by conventional methods therefrom. Other sources of this enzyme are strains of *Neisseria meningitides*, *Neisseria perflava* and other *Lactobacilli* strains.

Regarding the third reaction employed by the present invention:

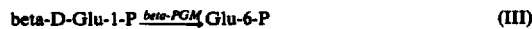

beta-D-Glu-1-P $\xrightarrow{beta-PGM}$ Glu-6-P    (III)

the enzyme beta-phosphoglucomutase (beta-PGM) catalyzes the conversion of beta-D-glucose-1-phosphate into Glucose-6-phsphate. Beta-phosphoglucomutase is present in at least about 100 IU per liter of reagent so that alpha-amylase of reaction I remains the rate-limiting constituent. It is preferred that about 500 IU of beta-PGM per liter of reagent be used when assaying alpha-amylase in human serum. The preferred source of beta-PGM is *Lactobacillus brevis* (ATCC8287). It is cultured and purified by conventional methods of enzyme purification. Other sources include strains of *Neisseria meningitides*, *Neisseria perflava* and *Euglena gracilis*.

It is preferred that glucose-1,6-diphosphate (Glu-1, 6-diP) be present in the enzyme system to act as a cofactor for beta-PGM. Beta-PGM requires that beta-form of Glu-1,6-diP for activity, but it is believed that the alpha-form of this co-factor may also work. The preferred concentration of Glu-1,6-diP should be at least about 0.01 grams per liter of reagent. The optimum concentration is about 0.075 gm per liter.

It is also preferred that divalent cations selected from the class consisting of $Mn^{+2}$, $Mg^{+2}$, $Co^{+2}$, $Zn^{+2}$ or $Ni^{+2}$ be present in the enzyme system to act as a cofactor for beta-PGM. The cations $Mn^{+2}$, $Mg^{+2}$, or $Co^{+2}$ are preferred over $Zn^{+2}$ or $Ni^{+2}$. The cation concentration should be at least about 1 millimole per liter of reagent and is preferably 8.4 millimoles per liter.

With respect to the fourth reaction employed in the present invention:

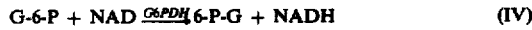

G-6-P + NAD $\xrightarrow{G6PDH}$ 6-P-G + NADH    (IV)

the glucose-6-phosphate is reacted with beta-nicotinamideadenine dinculeotide and G6PDH to produce 6-phosphogluconate and NADH.

The amount of NAD should be high enough to keep alpha-amylase the rate-limiting constituent. A suitable range for the NAD concentration is about 1 to about 10 millimoles per liter of reagent. The preferred concentration of NAD is about 2.5 millimoles. Beta-nicotinamide-adenine dinucleotide phosphate (NADP) may be substituted for NAD in the present invention.

The glucose-6-phosphate dehydrogenase (G-6-PDH) should also be present in a concentration of at least about 500 IU per liter of reagent so that this reaction is not the rate-limiting reaction. The preferred concentration of the G-6-PDH enzyme is about 5000 IU per liter of reagent. The preferred source of G-6-PDH is *Leuconostoc mesenteroides* (ATCC 12291) but it may be obtained from other sources.

In the preferred embodiment of the present invention, it is desirable to employ a fifth reaction as part of the assay:

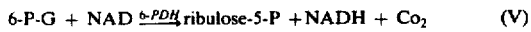

6-P-G + NAD $\xrightarrow{6\text{-}PDH}$ ribulose-5-P + NADH + Co$_2$ (V)

The purpose of this fifth reaction is to increase the sensitivty and accuracy of the assay by increasing the amount of NADH produced from the fourth reaction.

The minimum concentration of 6-PDH should be at least about 200 International Units per liter of reagent. The optimum concentration of 6-PDH is about 700 International Units per liter. The preferred source of this enqume is *Leuconostoc mesenteroides* (ATCC 12291), from which the enzyme has been cultured and purified by conventionally known methods, but it may be obtained from other sources.

Sodium chloride may be added to the reagent system to increase the activity of the alpha-amylase.

Buffers including Potassium Phosphate Dibasic ($K_2HPO_4$) and Monobasic ($KH_2PO_4$) can be used to obtain the optimum pH in which to carry out the reaction sequence. Non-phosphate buffers may be used, but are not preferred because phosphate buffers provide a source of phosphate ions. Exemplary of other buffers which were tested and found to be satisfactory are piperazine-N, $N^1$-bis (2-ethanesulfonic acid); tris (hydroxymethyl) amiomethane; N-2-hydroxyethylpiperazine-$N^1$-2-ethane sulfonic acid; and triethanolamine. Exemplary of other buffers which may also be satisfactory are N-(2-acetamido)iminodiacetic acid; N-(2-acetamido)-2-aminoethanesulfonic acid; and N,N-bis(2-hydroxyethyl)-2-aminoethanesulfonic acid.

The rate of NADH production and the conversion of such rate into the concentration of alpha-amylase is accomplished by known methods. One such method uses spectophotometric means to measure the change in absorbance of light due to the production of NADH at wave lengths ranging from about 300 to about 370 millimicrons (nm) at a temperature range of from about 15° to about 50° C. A wave length of about 340 nm at about 37° C is preferred.

When the rate of change in absorbance is measured, the concentration of alpha-amylase may be calculated by the following equation wherein the change in absorbance is measured at a wave length of 340 nm and a temperature of 37° C:

$$\text{IU/liter} = \frac{\Delta A \times V_t \times 1000}{V_s \times 6.22}$$

$\Delta A$ = change of absorbance/minute
$V_t$ = total reaction volume
$V_s$ = volume of sample containing alpha-amylase 6.22 = millimolar absorbtivity index of NADH at 340 nm

EXAMPLE 1

Ingredients of Assay Mixture for Alpha-Amylase

The following is the composition of the preferred reagent of the present invention prepared as a 1 liter solution of deionized water:

| | |
|---|---|
| Superlose 500 | 5.00 grams |
| Potassium Phosphate Dibasic | 2.65 grams |
| Potassium Phosphate Monobasic | 1.33 grams |
| Maltose Phosphorylase | 1000 IU |
| Beta-Phosphoglucomutase | 500 IU |
| NAD . $4H_2O$ | 1.8 grams |
| Glucose-6-Phosphate Dehydrogenase | 5000 IU |
| 6-Phosphogluconate Dehydrogenae | 700 IU |
| $MgCl_2 . 6H_2O$ | 1.7 grams |
| Sodium Chloride | 0.5 grams |
| G 1,6-diP | 0.075 grams |

The pH is adjusted to about 6.0 to about 7.5 with a pH of 6.5 being preferred.

The reagent system of the present invention may be stored and used in the form of an aqueous solution or the solution may be freeze dried by conventional means and reconstituted with water when ready for use. The reagent system may also be prepared using the constituents thereof in powdered form which are solubilized with water when ready for use.

The enzyme beta-amylase catalyzes a reaction similar to the first reaction (I), hydrolyzing alpha-1,4 linked glucan to beta-maltose.

In the case of a reagent system for a beta-amylase assay the only modification to the reagent system disclosed hereinabove would be the addition of the enzyme mutarotase to catalyze conversion of beta-maltose into alpha-maltose. The amount of said mutarotase addition would be at least about 2000 units per liter of reagent, with about 60,000 units being preferred.

The principles of the instant invention may also be applied to assays for phosphatases or for inorganic phosphate by omitting the constituents of the reagent system of the present invention which make the first reaction proceed and by making the following additional modifications to the reagent system:

In the case of a reagent system for an inorganic phosphate assay, starch and phosphate ion are omitted from the reagent system and maltose is added to the reagent. The amount of phosphate ion is determined by measuring the quantity of NADH produced by the coupled enzyme reactions of the instant invention. The reagent system is set forth hereinbelow and is based on 1 liter of reagent.

EXAMPLE 2

Ingredients of Assay Mixture for Inorganic Phosphate

| Ingredients | Preferred Amount | Minimum Amount Required |
|---|---|---|
| Maltose | 2.0 grams | about 0.5 grams |
| Maltose phosphorylase | 1000 IU | about 300 IU |
| Beta-phosphoglucomutase | 500 IU | about 150 IU |
| NAD . $4H_2O$ | 1.8 grams | about 0.4 grams |
| Glucose-6-phosphate dehydrogenase | 5000 IU | about 500 IU |
| $MgCl_2 . 6H_2O$ | 1.7 grams | about 0.2 grams |
| Glucose-1,6-diphosphate | 0.10 grams | about 0.02 grams |

| Ingredients | Preferred Amount | Minimum Amount Required |
|---|---|---|
| 1M Triethanolamine HCl buffer, pH 7.0 | 50 ml | about 10 ml |

The pH is adjusted to about 6.0 to about 8.0 with a pH of 7.0 being preferred.

In the case of a reagent system for an acid phosphatase assay, starch and phosphate ion are omitted from the reagent and alpha-naphthylphosphate and maltose are included in the reagent.

Alpha-naphthylphosphate is hydrolyzed by acid phosphatase to alpha-naphthol and phosphate ion. The rate of phosphate ion release is then determined by measuring the rate of NADH production utilizing the coupled enzymatic reactions of the instant invention. The reagent system is set forth hereinbelow and is based upon 1 liter of reagent.

EXAMPLE 3

Ingredients of Assay Mixture for Acid Phosphatase

| Ingredients | Preferred Amount | Minimum Amount Required |
|---|---|---|
| Alpha-naphthyl phosphate | 0.74 grams | about 0.3 grams |
| Maltose | 2.0 grams | about 0.5 grams |
| Maltose phosphorylase | 1000 IU | about 300 IU |
| Beta-phosphoglucomutase | 500 IU | about 150 IU |
| NAD . 4H$_2$O | 1.8 grams | about 0.4 grams |
| Glucose-6-phosphate dehydrogenase | 5000 IU | about 2000 IU |
| MgCl$_2$. 6H$_2$O | 1.7 grams | about 0.2 grams |
| Glucose 1,6-diphosphate | 0.10 grams | about 0.02 grams |
| 0.5M solution of sodium citrate | 100 ml | about 25 ml |

The pH is adjusted from about 4.5 to about 5.5 with a pH of 5.0 being preferred.

While the particular embodiment of the invention chosen herein for purposes of the disclosure is at present considered to be preferred, it is to be understood that the invention is intended to cover all changes and modifications in the disclosed embodiments which fall within the spirit and scope of the invention.

We claim:

1. An alpha-amylase assay comprising:
   a. performing simultaneous reactions which comprise:
      I. reacting a polysaccharide having glucose molecules primarily connected through alpha 1,4 linkages in the presence of an alpha-amylase specimen to form alpha-maltose;
      ii. reacting alpha-maltose with phosphate ions in the presence of maltose phosphorylase to form glucose and beta-D-glucose-1-phosphate;
      iii. reacting beta-D-glucose-1-phosphate in the presence of beta-D-pgosphoglucomutase to form glucose-6-phosphate; and
      iv. reacting glucose-6-phosphate in the presence of glucose-6-phosphate dehydrogenase and a co-enzyme selected from a group consisting of beta-nicotinamide-adenine dinucleotide, beta-nicotinamide-adenine-dinucleotide phosphate, and mixtures thereof to form the reduced form of said co-enzyme and 6-phosphogluconate; and
   b. measuring the rate of production of said reduced co-enzyme,
wherein the alpha-amylase being measured is rate-limiting.

2. The alpha-amylase assay of claim 1 wherein said beta-D-glucose-1-phosphate is reacted in the presence of beta-D-phosphoglucomutase and glucose-1,6-diphosphate to form glucose-6-phosphate.

3. The alpha-amylase assay of claim 2 further comprising:
   reacting 6-phosphogluconate in the presence of said co-enzyme and 6-phosphogluconate dehydrogenase to form the reduced form of said co-enzyme and ribulose-5-phosphate.

4. The alpha-amylase assay of claim 12 wherein said beta-D-glucose-1-phosphate is reacted in the presence of beta-D-phosphoglucomutase, glucose-1,6-diphosphate, and a cation selected from a group consisting of $Mn^{+2}$, $Mg^{+2}$, $Co^{+2}$, $Zn^{+2}$, $Ni^{+2}$, and mixtures thereof to form glucose-6-phosphate.

5. The alpha-amylase assay of claim 4 further comprising:
   reacting 6-phosphogluconate in the presence of said co-enzyme and 6-phosphogluconate dehydrogenase to form the reduced form of said co-enzyme and ribulose-5-phosphate.

6. The alpha-amylase assay of claim 5 wherein said cation is selected from the group consisting of $Mn^{+2}$, $Mg^{+2}$, $Co^{+2}$, and mixtures thereof.

7. The alpha-amylase assay of claim 6 wherein said simultaneous reactions are performed at a pH of from about 6 to about 7.5.

8. The alpha-amylase assay of claim 7 wherein said pH is about 6.5.

9. The alpha-amylase assay of claim 1 wherein said simultaneous reactions are performed at a pH of from about 6 to about 7.5.

10. The alpha-amylase assay of claim 9 wherein said pH is about 6.5.

11. A reagent system for an alpha-amylase assay comprising:
   a. a polysaccharide having glucose molecules primarily connected through alpha 1,4 linkages;
   b. phosphate ions,
   c. maltose phosphorylase;
   d. a co-enzyme selected from a group consisting of beta-nicotinamide-adenine dinucleotide, beta-nicotinamide-adenine dinucleotide phosphate, and mixtures thereof;
   e. glucose-6-phosphate dehydrogenase; and
   f. beta-D-phosphoglucomutase;
wherein the above are present in amounts such that the alpha amylase to be assayed is rate-limiting.

12. The reagent system of claim 11 further comprising glucose-1,6-diphosphate.

13. The reagent system of claim 12 further comprising 6-phosphogluconate dehydrogenase.

14. The reagent system of claim 12 further comprising a cation selected from a group consisting of $Mn^{+2}$, $Mg^{+2}$, $Co^{+2}$, $Zn^{+2}$, $Ni^{+2}$, and mixtures thereof.

15. The reagent system of claim 12 further comprising 6-phosphogluconate dehydrogenase and a cation selected from a group consisting of $Mn^{+2}$, $Mg^{+2}$, $Co^{+2}$, $Zn^{+2}$, $Ni^{+2}$, and mixtures thereof.

16. The reagent system of claim 15 wherein said cation is selected from the group consisting of $Mg^{+2}$, $Mn^{+2}$, $Co^{+2}$, and mixtures thereof.

17. The reagent system of claim 16 wherein said glucose-1,6-diphosphate consists essentially of the beta form thereof.

18. The reagent system of claim 17 wherein said polysaccharide is an alpha-1,4 glucan.

19. The reagent system of claim 18 wherein said alpha-1,4 glucan is starch.

20. A reagent system for an alpha-amylase assay wherein the alpha-amylase to be assayed is rate-limiting comprising per liter of reagent:
   a. at least about 1 gram of a polysaccharide having glucose molecules primarily connected through alpha 1,4 linkages;
   b. from about 0.01 to about 0.1 molar concentration of phosphate ions;
   c. at least about 200 International Units of maltose phosphorylase;
   d. at least about 1 millimole of a co-enzyme selected from a group consisting of beta-nicotinamide-adenine dinucleotide, beta-nicotinamide-adenine dinucleotide phosphate, and mixtures thereof;
   e. at least about 500 International Units of glucose-6-phosphate dehydrogenase; and
   f. at least about 100 International Units of beta-D-phosphoglucomutase.

21. The reagent system of claim 20 further comprising at least about 0.1 grams of glucose-1,6-diphosphate.

22. The reagent system of claim 21 further comprising at least about 200 International Units of 6-phosphogluconate dehydrogenase.

23. The reagent system of claim 21 further comprising at least one millimole of a cation selected from a group consisting of $Mn^{+2}$, $Mg^{+2}$, $Co^{+2}$, $Zn^{+2}$, $Ni^{+2}$, and mixtures thereof.

24. The reagent system of claim 20 comprising per liter of reagent:
   a. about 5 grams of starch;
   b. about 0.025 moles of phosphate ions;
   c. about 1000 International Units of maltose phosphorylase;
   d. about 2.5 millimole of said co-enzyme;
   e. about 5000 International Units of glucose-6-phosphate dehydrogenase;
   f. about 500 International Units of beta-phosphoglucomutase;
   g. about 0.075 grams of beta-glucose-1,6-diphosphate;
   h. about 1.7 grams of $MgCl_2.6H_2O$.

25. The reagent system of claim 24 further comprising about 700 International Units of phosphogluconate dehydrogenase.

26. A freeze dried reagent system for an alpha-amylase assay, said freeze dried reagent prepared from the reagent system set forth in claim 11.

27. A powdered reagent system for an alpha-amylase assay which when solubilized in water will produce the reagent system set forth in claim 11.

28. A kit comprising a plurality of reagents which when mixed together will produce the reagent system as set forth in claim 11.

29. The reagent system of claim 11 wherein said polysaccharide is a maltooligosaccharide.

30. The reagent system of claim 29 wherein said maltooligosaccharide is selected from a group consisting of maltotetraose and maltopentaose.

31. The reagent system of claim 30 wherein said maltooligosaccharide is maltotetraose.

32. The reagent system of claim 17 wherein said polysaccharide is a maltooligosaccharide.

33. The reagent system of claim 32 wherein said maltooligosaccharide is selected from a group consisting of maltotetraose and maltopentaose.

34. The reagent system of claim 33 wherein said maltooligosaccharide is maltotetraose.

35. The reagent system of claim 20 wherein said polysaccharide is a maltooligosaccharide.

36. The reagent system of claim 35 wherein said maltooligosaccharide is selected from a group consisting of maltotetraose and maltopentaose.

37. The reagent system of claim 36 wherein said maltooligosaccharide is maltotetraose.

* * * * *